US010758902B2

(12) United States Patent
Hofmeister et al.

(10) Patent No.: US 10,758,902 B2
(45) Date of Patent: Sep. 1, 2020

(54) METHOD OF FABRICATING SEMIPERMEABLE ULTRATHIN POLYMER MEMBRANES

(71) Applicant: Ultra Small Fibers, LLC, Wartrace, TN (US)

(72) Inventors: William Hudson Hofmeister, Nashville, TN (US); Alexander Yuryevich Terekhov, Estill Springs, TN (US); Jose Lino Vasconcelos da Costa, Murfreesboro, TN (US)

(73) Assignee: Ultra Small Fibers, LLC, Wartrace, TN (US)

( * ) Notice: Subject to any disclaimer, the term of this patent is extended or adjusted under 35 U.S.C. 154(b) by 423 days.

(21) Appl. No.: 15/585,424

(22) Filed: May 3, 2017

(65) Prior Publication Data

US 2017/0320057 A1    Nov. 9, 2017

Related U.S. Application Data

(60) Provisional application No. 62/331,077, filed on May 3, 2016.

(51) Int. Cl.
*B01D 69/12* (2006.01)
*C08J 5/18* (2006.01)
(Continued)

(52) U.S. Cl.
CPC ........ *B01L 3/502707* (2013.01); *B01D 69/12* (2013.01); *B01D 69/122* (2013.01);
(Continued)

(58) Field of Classification Search
None
See application file for complete search history.

(56) References Cited

U.S. PATENT DOCUMENTS

| 5,356,936 A | 10/1994 | Howell et al. | |
| 8,828,239 B2 * | 9/2014 | Peng | B01D 67/0006 210/702 |

(Continued)

FOREIGN PATENT DOCUMENTS

| KR | 101295826 B1 | 8/2013 |
| KR | 20130142090 A | 12/2013 |

OTHER PUBLICATIONS

Chen, L. et al. "Polymeric micro-filter manufactured by a dissolving mold technique," 2010 J. Micromech. Microeng. 20, 075005 (6 pages) (Year: 2010).*

(Continued)

*Primary Examiner* — Christopher Adam Hixson
*Assistant Examiner* — Michelle Adams
(74) *Attorney, Agent, or Firm* — Eric B. Fugett; Mark A. Pitchford; Pitchford Fugett, PLLC

(57) ABSTRACT

A semipermeable ultrathin polymer membrane comprises a substantially optically transparent polymer film having a surface area to thickness ratio of at least 1,000,000:1, and an array of precisely spatially ordered pores of a user-selected diameter defined therethrough. Such membranes can be fabricated by providing a mold having a patterned array of nanoholes femtosecond laser ablated in a surface thereof; applying a first polymer solution onto the mold surface so that the first polymer solution infiltrates the nanoholes; allowing the first polymer solution to dry and form a replica of the mold having a plurality of freestanding nanoneedles extending from a surface of the replica; removing the replica from the mold; coating the replica surface with a second polymer solution; drying the second polymer solution to form a porous polymer film; and dissolving the replica in a solvent to release the film from the replica as a semipermeable ultrathin polymer membrane.

2 Claims, 6 Drawing Sheets

(4 of 6 Drawing Sheet(s) Filed in Color)

(51) Int. Cl.

| | |
|---|---|
| B01L 3/00 | (2006.01) |
| B29D 99/00 | (2010.01) |
| G01N 33/52 | (2006.01) |
| B05D 1/00 | (2006.01) |
| B29C 37/00 | (2006.01) |
| B29C 41/02 | (2006.01) |
| B29C 41/38 | (2006.01) |
| B32B 3/26 | (2006.01) |
| B32B 27/30 | (2006.01) |
| G01N 33/50 | (2006.01) |
| B32B 37/24 | (2006.01) |
| B32B 37/12 | (2006.01) |
| B32B 38/10 | (2006.01) |
| B29K 67/00 | (2006.01) |
| B29K 629/00 | (2006.01) |
| B29L 31/00 | (2006.01) |
| B32B 38/00 | (2006.01) |

(52) U.S. Cl.
CPC ... *B01L 3/502715* (2013.01); *B01L 3/502753* (2013.01); *B05D 1/005* (2013.01); *B29C 37/0067* (2013.01); *B29C 41/02* (2013.01); *B29C 41/38* (2013.01); *B29D 99/005* (2013.01); *B32B 3/266* (2013.01); *B32B 27/306* (2013.01); *C08J 5/18* (2013.01); *G01N 33/5005* (2013.01); *G01N 33/525* (2013.01); *B01L 2200/12* (2013.01); *B01L 2300/0819* (2013.01); *B01L 2300/0887* (2013.01); *B01L 2300/161* (2013.01); *B01L 2300/168* (2013.01); *B29K 2067/046* (2013.01); *B29K 2629/04* (2013.01); *B29K 2995/0026* (2013.01); *B29L 2031/755* (2013.01); *B32B 37/12* (2013.01); *B32B 38/0008* (2013.01); *B32B 38/10* (2013.01); *B32B 2037/243* (2013.01); *C08J 2367/04* (2013.01)

(56) References Cited

U.S. PATENT DOCUMENTS

| | | | |
|---|---|---|---|
| 8,956,696 B2 | 2/2015 | Wolcott et al. | |
| 2011/0189440 A1* | 8/2011 | Appleby | B22C 9/10 428/156 |
| 2013/0216779 A1* | 8/2013 | Hofmeister | G03F 7/0002 428/141 |
| 2018/0298317 A1* | 10/2018 | Ingber | C12M 23/16 |

OTHER PUBLICATIONS

Wei, H. et al. "Particle sorting using a porous membrane in a microfluidic device," Lab Chip, 2011,11, 238-245, including Electronic Supplementary Information. (Year: 2011).*
Selvam, S. et al. "Microporous Poly(L-Lactic Acid) Membranes Fabricated by Polyethylene Glycol Solvent-Cast/Particulate Leaching Technique," Tissue Eng Part C Methods. Sep. 2009; 15(3): 463-474. (Year: 2009).*
Rosas Escobar, J.M. "Fabrication of a microporous PDMS membrane for an Organ-on-Chip device," Master of Science Thesis, Delft University of Technology, Nov. 7, 2014. (Year: 2014).*
(Male, K) Artificial alveolar-capillary membrane on a microchip, A project report, California Polytechnic Slate University, San Luis Obispo, California. Jun. 1, 2012. [Retrieved from the Internet on Jun. 7, 2017]. <URL: http://digitalcommons.calpoly.edu/cgi/vIewcontent.cgi?artIcle=10548,context=matesp>; abstract: pp. 2, 4-6, 8-13.
(Esch, MB et al) On chip porous polymer membranes for integration of gastrointestinal tract epithelium with microfiuidic 'body-on-a-chip' devices. Biomedical Microdevices, vol. 14, pp. 895-906. Jul. 31, 2012; title; abstract: pp. 896-897, 899, 904.
(Rajput, D et al. ), Solution-Cast High-Aspect-Ratio Polymer Structures from Direct-Write Templates. ACS Applied Materials and Interfaces, vol. 5, No. 1; Dec. 26, 2012; abstract; pp. A-C.
(Epshteyn, A) Design and fabrication of a membrane integrated microfluidic cell culture device suitable for high-resolution imaging, A Thesis, College or Engineering, University of South Florida, Dec. 31, 2010. [Retrieved from the internet on Jun. 7, 2017). <URL:http://scholarcommons.usf.edu/cgi/viewcontent.cgi?article=47 12&context=etd>; pp. 33-34,37,42.
(Yang, J et al. ). Fabrication and surface modification of macroporous poly(L-lactic acid) and poly(L-lactic-co-glycolic acid) (70/30) cell scaffolds for human skin fibroblas t cell culture. Journal of Biomedical Materials Research Part A, vol. 52, No. 3, pp. 438-446. Dec. 5, 2002; pp. 439-440.
(Pensabene, Vet al.) Ultrathin Polymer Membranes with Patterned, Micrometric Pores for Organs-on-Chips. ACS Applied Materials and Interfaces. vol. 8, No. 34. Aug. 11, 2016; abstract.
PCT/US17/30883 International Search Report and Written Opinion, dated Aug. 22, 2017, 12 pages.
Boyden, S., The chemotactic effect of mixtures of antibody and antigen on polymorphonuclear leucocytes. The Journal of Experimental Medicine 1962, 115 (3), 453-466.
Ingber, D. E., Reverse Engineering Human Pathophysiology with Organson-Chips. Cell 164 (6), 1105-1109, Mar. 10 , 2016.
Huh, D.; Hamilton, G. A; Ingber, D. E., From 3D cell culture to organson- chips. Trends in Cell Biology 21 (12), 745-754, (2011).
McCaffrey, L M.; Macara, I. G., Epithelial organization, cell polarity and tumorigenesis. Trends in Cell Biology 21 (12), 727-735.
Okamura, Y.; Kabata, K.; Kinoshita, M.; Saitoh, D.; Takeoka, S., Free-Standing Biodegradable Poly(lactic acid) Nanosheet for Sealing Operations in Surgery. Advanced Materials 2009, 21 (43), 4388.
Fujie, T.; Okamura, Y.; Takeoka, S., Selective surface modification of free-standing polysaccharide nanosheet with micro/nano-particles identified by structural color changes. Colloids and Surfaces A: Physicochemical and Engineering Aspects 2009, 334 (1-3), 28-33.
Markutsya, S.; Jiang, C. Y.; Pikus, Y.; Tsukruk, V. V., Freely suspended layer-by-layer nanomembranes: Testing micromechanical properties. Advanced Functional Materials 2005, 15 (5), 771-780.
Zucca, A; Yamagishi, K; Fujie, T.; Takeoka, S.; Mattoli, V.; Greco, F., Roll to roll processing ofultraconformable conducting polymer nanosheets. Journal of Materials Chemistry C 2015, 3 (25), 6539-6548.
Taccola, S.; Desii, A; Pensabene, V.; Fujie, T.; Saito, A; Takeoka, S.; Dario, P.; Menciassi, A; Mattoli, V., Free-Standing Poly(L-lactic acid) Nanofilms Loaded with Superparamagnetic Nanoparticles. Langmuir 2011, 27 (9), 5589-5595.
Jiang, C. Y.; Tsukruk, V. V., Freestanding nanostructures via layer-by layer assembly. Advanced Materials 2006, 18 (7), 829-840.
Endo, H.; Kado, Y.; Mitsuishi, M.; Miyashita, T., Fabrication of freestanding hybrid nanosheets organized with polymer Langmuir-Blodgett films and gold nanoparticles. Macromolecules 2006, 39 (16), 5559-5563.
Cho, J.; Char, K.; Hong, J. D.; Lee, K. B., Fabrication of highly ordered multilayer films using a spin self-assembly method. Advanced Materials 2001, 13 (14), 1076.
Ricotti, L.; Taccola, S.; Pensabene, V.; Mattoli, V.; Fujie, T.; Takeoka, S.; Menciassi, A; Dario, P., Adhesion and proliferation of skeletal muscle cells on single layer poly(lactic acid) ultra-thin films. Biomedical Microdevices 2010, 12(5), 809-819 11 p.
Ricotti, L.; Taccola, S.; Bemardeschi, I.; Pensabene, V.; Dario, P.; Menciassi, A, Quantification of growth and differentiation of C2Cl2 skeletal muscle cells on PSS-P AH-based polyelectrolyte layer-by-layer nanofilms. Biomedical Materials 2011, 6 (3).
Kim, H. J.; Ingber, D. E., Gut-on-a-Chip microenvironment induces human intestinal cells to undergo villus differentiation. Integrative Biology 2013, 5 (9), 1130-1140.
Kim, H. J.; Huh, D.; Hamilton, G.; Ingber, D. E, Human gut-on-a-chip inhabited by microbial flora that experiences intestinal peristalsis-like motions and flow. Lab on a Chip 2012, 12 (12), 2165-2174.

(56) References Cited

OTHER PUBLICATIONS

Booth, R.; Kim, H., Characterization of a microfluidic in vitro model of the blood-brain barrier (mu BBB). Lab on a Chip 2012, 12 (10), 1784-1792.

Esch, M. B.; Sung, J. H.; Yang, J.; Yu, C. H.; Yu, J. J.; Mar., J. C.; Shuler, M. L., On chip porous polymer membranes or integration of gastrointestinal tract epithelium with microfluidic 'body-on-a-chip' devices. Biomedical Microdevices 2012, 14 (5), 895-906.

Ulbricht, M., Advanced functional polymer membranes. Polymer 2006, 47 (7), 2217-2262.

Uragami, T.; Naito, Y.; Sugihara, M., Studies on synthesis and permeability of special polymer membranes .39. permeation characteristics and structure of polymer blend membranes from poly(vinylidene fluoride) and poly(ethylene glycol). Polymer Bulletin 1981, 4 (10), 617-622.

Marint, C. R.; Nishizawa, M.; Jirage, K.; Kang, M., Investigations of the transport properties of gold nanotubule membranes. Journal of Physical Chemistry B 2001, 105 (10), 1925-1934.

Kim, M. J.; Wanunu, M.; Bell, D. C.; Meller, A, Rapid fabrication of uniformly sized nanopores and nanopore arrays for parallel DNA analysis. Advanced Materials 2006, 18 (23), 3149.

Kuiper, S.; van Rijn, C. J. M.; Nijdam, W.; Elwenspoek, M. C., Development and applications of very high flux microfiltration membranes. Journal of Membrane Science 1998, 150 (1), 1-8.

Adiga S.P.; Jin,C M.; Curtiss, L.A; Monteiro-Riviere, N. A; Narayan, R. J., Nanoporous membranes for medical and biolodicai applications. Wiley Interdisciplinary Reviews-Nanomedicine and Nanobiotechnology 2009, I (5), 568-581.

White, Y. V.; Li, X. X.; Sikorski, Z.; Davis, L. M.; Hofmeister, W., Single-pulse ultrafast-laser machining of high aspect nano-holes at the surface of Si02. Optics Express 2008, 16 (19), 14411-14420.

Rajput, D.; Costa, L; Lansford, K.; Terekhov, A; Hofmeister, W., Solution-Cast High-Aspect-Ratio Polymer Structures Tom Direct-Write Templates. ACS Appl. Mater Interfaces 2013, 5 (1), 1-5.

Forrest, J.A., et al., Effect of Free Surfaces on the Glass Transition Temperature of Thin Polymer Films. Phys. Rev. Letters. 1996, vol. 77, No. 10, pp. 2002-2005.

Baudin, B.; Bruneel, A; Bosselut, N.; Vaubourdolle, M., A protocol for isolation and culture of human umbilical vein endothelial cells. Nature Protocols 2007, 2 (3), 481-485.

Pensabene, V.; Patel, P. P.; Williams, P.; Cooper, T. L; Kirkbride, K. C.; Giorgio, T. D.; Tulipan, N. B., Repairing Fetal Membranes with a Self-adhesive Ultrathin Polymeric Film: Evaluation in Midgestational Rabbit Model. Annals of Biomedical Engineering 2015, 43 (8), 1978-1988.

Jeong, J. W.; Yeo, W. H.; Akhtar, A; Norton, J. J. S.; Kwack, Y. J.; Li, S.; Jung, S. Y.; Su, Y. W.; Lee, W.; Xia, J.; Cheng, H. Y.; Huang, Y. G.; Choi, W. S.; Bretl, T.; Rogers, J. A, Materials and Optimized Designs for Human-Machine Interfaces Via Epidermal Electronics. Advanced Materials 2013, 25 (47), 6839-6846.

Ganan-Calvo, Alfonso M. et al, Focusing Capillary Jets Close to the Continuum Limit; 2007 Nature Publishing Group, seven pages.

St. Johnston, Daniel et al, Epithelial polarity and morphogensis, ScienceDirect, Current Opinion in Cell Biology 2011, 23:pp. 540-546, www.sciencedirect.com, seven pages.

Kim, Yohan et al, Quantification of Cancer Cell Extravasation in Vivo; Nature Protocols, vol. 11 No. 5, 2016 Macmillan Publishers Limited, twelve pages.

Li, Naichao et al, Conical Nanopore Membranes, Preparation and Transport Properties, Analytical Chemistry, Apr. 1, 2004, vol. 76, No. 7, pp. 2025-2030, Department of Chemistry and Center for Research at the Bio/Nano, University of Florida, Gainesville, FL 32611, six pages.

Okamura, Yosuke et al, Free-Standing Biodegradable Poly(lactic acid) Nanosheet for Sealing Operation in Surgery; Advanced Materials, two pages, Supporting Information . (2009).

Song, Jeremy J. et al, Organ Engineering Based on Decellularized Matrix Scaffolds, Cell Press, Department of Surgery, Massachusetts General Hospital, Harvard Medical School; 2011 Elsevier Ltd., Trends in Molecular Medicine, Aug. 2011, vol. 17, No. 8, nine pages.

Yamada, Kenneth M. et al, Modeling Tissue Morphogenesis and Cancer in 3D; Leading Edge Review; Cell 130, Aug. 24, 2007; 2007 Elsevier Inc., ten pages.

Zucca, A.; Cipriani, C.; Sudha; Tarantino, S.; Ricci, D.; Mattoli, V.; Greco, F., Tattoo Conductive Polymer Nanosheets for Skin-Contact Applications. Advanced Healthcare Materials 2015, 4 (7), 983-990.

\* cited by examiner

METHOD OF FABRICATING SEMIPERMEABLE ULTRATHIN POLYMER MEMBRANES

CROSS-REFERENCES TO RELATED APPLICATIONS

This application claims priority to U.S. Provisional Patent Application Ser. No. 62/331,077, entitled "Preparation of an ultrathin perfusion membrane with micron diameter pores from femtosecond laser machined template transfer process," filed May 3, 2016, the entire disclosure of which is hereby incorporated herein by this reference.

STATEMENT REGARDING FEDERALLY SPONSORED RESEARCH OR DEVELOPMENT

Subject matter described herein was supported in part by the Tennessee Higher Education Commission through a grant to the Center for Laser Applications, University of Tennessee Space Institute, and in part by the National Center for Advancing Translational Sciences of the NIH under Award No. UH2TR000491. The government may have certain rights in the subject matter disclosed herein.

REFERENCE TO SEQUENCE LISTING OR COMPUTER PROGRAM LISTING APPENDIX

Not Applicable.

BACKGROUND OF THE INVENTION

The present disclosure relates generally to semipermeable membranes, in particular very thin membranes with nonrandom pores, and more particularly to tunable polymer nanofilm perfusion membranes, which are believed to be advantageous for use in microfluidic devices for cell biology studies.

The basal lamina or basement membrane is a key physiological system that supports diverse epithelial cell types and participates in physicochemical signaling and transport between tissue types [4]. Its formation and function are essential in tissue maintenance, growth, angiogenesis, disease progression, and immunology.

In vitro models of the basement membrane, such as Boyden and transwell chambers, are essential to cell biology studies and are common in lab-on-a-chip devices where cells require apical and basolateral polarization. Extravasation, intravasation, membrane transport of chemokines, cytokines, chemotaxis of cells, and other key functions are routinely studied using these models. For example, transwells have been widely adopted for perfused, polarized cells, and migration assays since Boyden's initial chemotaxis experiment [1].

The promise of organs-on-a-chip technology (i.e., 3-D microfluidic cell culture chips that simulate the activities, mechanics, and physiological response of entire organs and/or organ systems) is essentially to create a more robust in vitro model of the complex electrophysicochemical systems that control cell function and fate in multicellular organisms [2]. However, a key element of any such model, including both static transwells and complex microfluidic organ models, is the semipermeable membrane used to simulate the basement membrane [3].

Critical properties of a semipermeable membrane suitable for use in a microfluidic device include controlled porosity, high species flux, mechanical strength, surface biocompatibility, and optical transparency. Although semi-permeable membranes formed from polycarbonate (PC) and polyester (PE) have traditionally been used for transwell cell culture and diffusion experiments, such membranes are far thicker than the basement membrane. Transwell membranes are typically more than 100 microns thick and the basement membrane is much less than one micron thick, typically tens of nanometers, three to four orders of magnitude thinner than currently available polycarbonate and polyester membranes, the transparency of which is not optimal in bright field light and confounds observation by differential interference contrast.

By contrast, ultrathin polymer films having a thickness of less than one micron (referred to herein as "nanofilms") are promising candidates for use as an in vitro model of the basement membrane because they are closer in thickness to native basement membrane and are compatible with cell culture. Nanofilms with thicknesses ranging from tens to hundreds of nanometers belong to a class of polymeric nanomaterials having huge surface to thickness ratios ($>10^6$), unique thickness-dependent interfacial and mechanical properties, and optical transparency. Previous studies have revealed that such films can have non-covalent high adhesiveness to surfaces, tunable flexibility and molecular permeability [5], defined structural color [6] and mechanical strength [7], and possibly conductive [8] and magnetic [9] properties, all of which enable such nanofilms to closely mimic the lamina basalis of the extracellular matrix in human tissues, making such films an ideal structure to direct cellular organization and regulate organ regeneration and function in vitro.

Nanofilm fabrication techniques are diverse, and include layer-by-layer assembly [10] methods, and the Langmuir-Blodgett method [11], among others. However, the simplest route to fabricate freestanding and easy-to-handle nanofilms is spin coating from a liquid polymer-solvent solution [12]. In previous works, full characterization of plain nanofilm structures was performed. The adhesion and proliferation of different cell types on poly (lactic acid) ("PLLA") nanofilms [13] and polyelectrolytic films [14] was confirmed.

Existing examples of organs-on-a-chip have used perforated polydimethylsiloxane ("PDMS") membranes [15, 16], polycarbonate [17] or photoresist membranes [18]. While the PDMS membranes have the advantages of optical transparency, tunable elastic modulus, and can be easily integrated in a monolithic PDMS device, it is still difficult to reduce the thickness of the membrane below 5 μm. This represents a major drawback of PDMS membranes because submicron membrane thickness is essential for physical contact and paracrine communication between cells growing on both sides.

Numerous approaches have been used to fabricate organic semipermeable membranes [19], such as polymer synthesis [20] and ion track etching of polymers [21]. However, these methods have numerous drawbacks mainly related to random arrangement of pores with wide size distribution or nanometric pore size. Other methods are based on direct micro- and nanofabrication on the plain polymer sheet, by e-beam lithography and by focused ion beam milling [22, 23]. These approaches have the advantage of control of the design and arrangement of the pores [24], but they also present drawbacks, such as long working time and seriality, and thus high cost.

Moreover, while direct etching of any polymeric film should be theoretically possible for example by tuning current and voltage of an ion or electron beam [24], it is practically impossible to drill holes with micrometric diameter through an approximately 100 nm thin film because the Gaussian distribution of the ion beam and the control of current and milling depth are not sufficient to avoid local polymer melting. Debris from the milling process limits the depth to 10× the diameter of the hole. Furthermore, direct milling of the film would implicate local changes in the film's mechanical and structural characteristics and thus increase the risk of breakage and tears in the polymer film.

Accordingly, what is needed are improvements in semipermeable membranes for use in microfluidic devices.

BRIEF SUMMARY OF THE INVENTION

The presently disclosed subject matter overcomes some or all of the above-identified deficiencies of the prior art, as will become evident to those of ordinary skill in the art after a study of the information provided in this document.

Disclosed herein are engineered semipermeable ultrathin polymer membranes, methods for the fabrication of same, and microfluidic devices comprising such membranes. The semipermeable membranes disclosed herein are advantageously transparent and include precisely patterned micrometric pores, enabling them to function as support for growth of cell layers as well as a separation between distinct microfluidic chambers. As such, they are expected to be of significant utility in cellular assays, chemotaxis studies, and organs-on-a-chip applications.

The semipermeable membranes disclosed herein can be formed by spin coating-assisted deposition of a polymer-solvent solution such as PLLA atop a sacrificial array of spatially ordered polyvinyl-alcohol ("PVA") nanoneedles, followed by removal of the sacrificial PVA nanoneedle array. The PVA nanoneedles are formed by PVA replication of an array of surface nanometric holes formed on a fused silica wafer using femtosecond laser machining.

Accordingly, in one aspect, the disclosure provides a method of fabricating a semipermeable ultrathin polymer membrane, comprising providing a mold having a patterned array of nanoholes femtosecond laser ablated in a surface thereof; applying a first polymer solution onto the mold surface so that the first polymer solution infiltrates the nanoholes; allowing the first polymer solution to dry and form a negative replica of the mold, the replica having a first surface, a second surface opposite the first surface, and a plurality of freestanding nanoneedles extending a nanoneedle height from the first surface; removing the replica from the mold; coating the first replica surface with a second polymer solution whereby the first replica surface is covered with a layer of the second polymer solution having a thickness that is less than the nanoneedle height such that the nanoneedles extend through said layer above a surface of the layer of second polymer solution; drying the second polymer solution to form a porous polymer film; and dissolving the replica in a solvent to release the film from the replica as a semipermeable ultrathin polymer membrane.

In another aspect, the disclosure provides a semipermeable ultrathin polymer membrane comprising an optically transparent polymer film having a surface area to thickness ratio of at least 1,000,000:1, and an array of spatially ordered pores having a preselected micrometric diameter defined therethrough.

In yet another aspect, the disclosure provides a microfluidic device for studying cell biology in vitro, comprising a first microfluidic layer having an upper surface, a lower surface, an apical chamber defined in the lower surface, and an aperture in fluid communication with the apical chamber extending through the upper surface; a second microfluidic layer having an upper surface, a lower surface, and at least one basal chamber defined in the upper surface; and an optically transparent, biocompatible polymer nanofilm having an upper surface, a lower surface, a surface area to thickness ratio of at least 1,000,000:1, and an ordered array of micrometric pores defined therethrough, the film contacting the lower surface of the first microfluidic layer over the apical chamber and the upper surface of the second microfluidic chamber over the basal chamber such that the apical chamber is in fluid communication with the basal chamber through the pores of the film.

Numerous other objects, advantages and features of the present disclosure will be readily apparent to those of skill in the art upon a review of the following drawings and description of a preferred embodiment.

BRIEF DESCRIPTION OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

Figure 1:
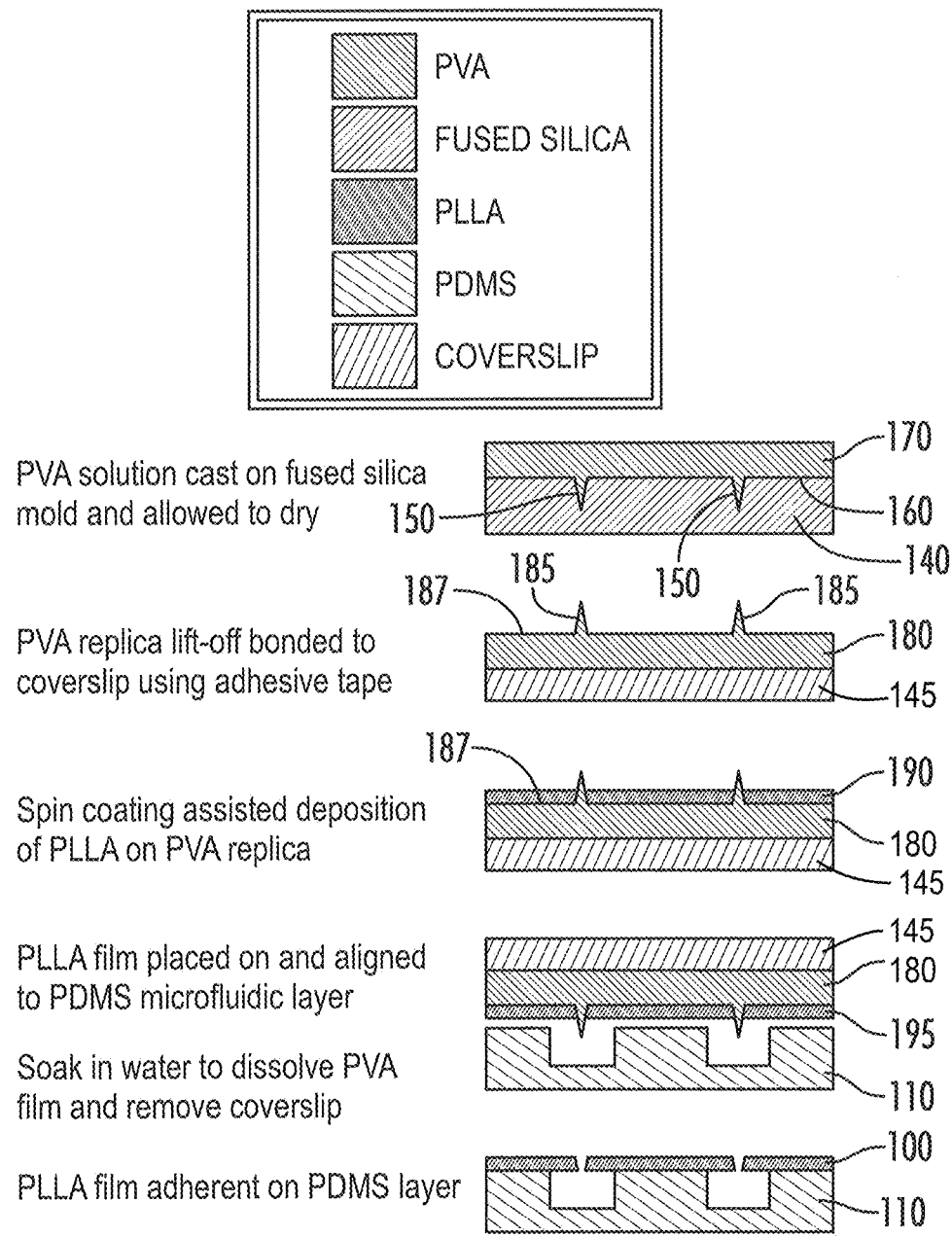
FIG. 1 depicts an embodiment of a method of fabricating a semipermeable ultrathin membrane 100 from PLLA.

The details of one or more embodiments of the presently disclosed subject matter are set forth in this document. Modifications to embodiments described in this document, and other embodiments, will be evident to those of ordinary skill in the art after a study of the information provided herein. The information provided in this document, and particularly the specific details of the described exemplary embodiments, is provided primarily for clearness of understanding and no unnecessary limitations are to be understood therefrom. In case of conflict, the specification of this document, including definitions, will control.

While the terms used herein are believed to be well understood by one of ordinary skill in the art, definitions are set forth herein to facilitate explanation of the subject matter disclosed herein.

Unless define otherwise, all technical and scientific terms used herein have the same meaning as commonly understood by one of ordinary skill in the art to which the subject matter disclosed herein belongs. Although any methods, devices, and materials similar or equivalent to those described herein can be used in the practice or testing of the presently disclosed subject matter, representative methods, devices and materials are now described.

The terms "a", "an", and "the" refer to "one or more" when used in this application, including the claims. Thus, for example, reference to "a contaminant" includes a plurality of particles of the contaminant, and so forth. The use of the word "a" or "an" when used in conjunction with the term "comprising" in the claims and/or the specification may mean "one," but it is also consistent with the meaning of "one or more," "at least one," and "one or more than one."

All references to singular characteristics or limitations of the present disclosure shall include the corresponding plural characteristic(s) or limitation(s) and vice versa, unless otherwise specified or clearly implied to the contrary by the context in which the reference is made.

All combinations of method or process steps as used herein can be performed in any order, unless otherwise specified or clearly implied to the contrary by the context in which the referenced combination is made.

The methods and devices of the present disclosure, including components thereof, can comprise, consist of, or consist essentially of the essential elements and limitations of the embodiments described herein, as well as any additional or optional components or limitations described herein or otherwise useful.

Unless otherwise indicated, all numbers expressing physical dimensions, quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently disclosed subject matter.

As used herein, the term "about," when referring to a value or to an amount of mass, weight, time, volume, concentration, percentage or a physical dimension such as length, width, or diameter, is meant to encompass variations of in some embodiments ±20%, in some embodiments ±10%, in some embodiments ±5%, in some embodiments ±1%, in some embodiments ±0.5%, and in some embodiments ±0.1% from the specified value or amount, as such variations are appropriate to perform the disclosed methods.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

For purposes of clarity, the term "nanohole" is used herein to refer to a minute opening or aperture (commonly referred to as a hole or pore) that has been laser ablated into the surface of a substrate. In some embodiment, a nanohole has a diameter less than 1 µm. By contrast, the term "pore" is used herein to refer to a minute opening or aperture extending through a semipermeable membrane formed in accordance with the present disclosure.

As used herein, the term "semipermeable membrane" refers to a nanofilm with an array of ordered pores of a specific user-defined size, distribution, and shape; precisely patterned and extending completely through the nanofilm to allow passage of chemical species and cells of a specific preselected size range, while blocking migration of other chemical species and cells outside the specific preselected size range. The term "array" as used herein refers to a plurality of structures (such as nanoholes, pores, and nanoneedles) having user-defined physical dimensions and spatial parameters.

User-tunable physical characteristics of the semipermeable membranes disclosed herein include pore spacing, pore diameter, number of pores per unit of surface area, membrane thickness, and membrane constituent material. For example, semipermeable membranes disclosed herein can comprise millions of pores per square centimeter of surface area, with pore diameter and spacing, composition configured to allow passage of chemical species and cells of a specific preselected size range, while blocking migration of other chemical species and cells outside the specific preselected size range. In some embodiments, one or more of pore surface area density, diameter, spacing, and shape are selected to perform a perfusion function. In certain embodiments, the semipermeable membranes can be optimized or "tuned" to perform a specific perfusion function or target a preselected chemical species or cells or protein size.

The semipermeable membranes disclosed herein can include pores spaced along an X-axis and a Y-axis at the same or different intervals along either axis. In some embodiments, the pores can be spaced from about 1 μm to about 100 μm apart on one or both of the X-axis and the Y-axis. In some embodiments, the pores can be spaced from about 5 μm to about 10 μm apart on one or both of the X-axis and the Y-axis. In still some embodiments, the pores can be spaced about 2 μm apart on one or both of the X-axis and the Y-axis. In some embodiments advantageous to the study of cell migration or chemotaxis, the pores may be spaced as far as about 100 μm apart. However, using the methods disclosed herein, it is possible to fabricate semipermeable membranes having pores spaced as closely as about 1 μm apart.

In some embodiments, a semipermeable membrane disclosed herein can include pores having an average diameter of from about 100 nm to about 3 μm. In certain embodiments, a semipermeable membrane disclosed herein can include pores having an average diameter of from about 300 nm to about 2 μm.

Replicas of individual nanoholes are referred to herein as "nanoneedles." As used herein, the term "nanoneedle" refers to a nanostructure having a diameter of less than 1000 nanometers for more than half the length of the structure. In some embodiments, the nanoneedles disclosed herein can comprise a tapered base portion and a relatively longer fiber portion which extends from the base portion to a terminal tip. In such embodiments, the fiber portion has a diameter of less than 1000 nm and a length greater than that of the base portion, and the base portion can have a diameter of from about 4.0 μm to less than 1.0 μm. Additionally, in some embodiments, the base portion can also have a length of from about 1.0 μm to about 10 μm, and the fiber portion can have a length of from about 10 to 100 times greater than the length of the base portion.

Semipermeable membranes disclosed herein can be composed of virtually any biocompatible polymer that is not water soluble. Non-limiting examples of suitable polymers include poly(ε-caprolactone) (PCL), polyethylene oxide (PEO), polyvinyl chloride (PVC), polyvinyl formal (PVF), polyisoprene, trans (PI), polypropylene (PP), low-density polyethylene (LDPE), high-density polyethylene (HDPE), polyvinylidene fluoride (PVDF), poly-lactic acid (PLA), and poly-L-lactic acid (PLLA). It should be understood that a blend of two or more such polymers can also be used.

The presently disclosed subject matter is further illustrated by the following specific but non-limiting example. The following example may include compilations of data that are representative of data gathered at various times during the course of development and experimentation related to the present invention.

Example 1

The goal of the present study was to integrate a semipermeable ultrathin polymer membrane with precisely positioned pores of 2 μm diameter in a microfluidic device with apical and basolateral chambers. We selected poly (L-lactic acid) ("PLLA"), a transparent biocompatible polymer, to prepare the semipermeable ultrathin membranes. The pores were generated by pattern transfer using a three-step method coupling femtosecond laser machining, polymer replication, and spin coating. Each step of the fabrication process was characterized by scanning electron microscopy to investigate reliability of the process and fidelity of pattern transfer.

In order to evaluate the compatibility of the fabrication method with organs-on-a-chip technology, porous PLLA membranes were embedded in polydimethylsiloxane ("PDMS") microfluidic devices and used to grow human umbilical vein endothelial cells ("HUVECS") on top of the membrane with perfusion through the basolateral chamber. Viability of cells, optical transparency of membranes, and strong adhesion of PLLA to PDMS were observed, thus confirming the suitability of the prepared membranes for use in organs-on-a-chip.

Materials and Methods

Fabrication of Fused Silica Molds

A 10 mm×10 mm regular array of 201×201 nanoholes 150 was patterned on the surface 160 of a 500 μm thick UV grade fused silica wafer 140 (Mark Optics, Inc.) using the single-pulse femtosecond laser machining technique first described by White, et al. [25]. In their 2008 paper, White and co-workers demonstrated that high numerical aperture single-pulse femtosecond laser machining can create uniquely-shaped nanoholes at the surface of fused silica, exhibiting high aspect ratios, with depths that exceed 10 μm and diameters below 200 nm. In the present work, femtosecond laser machining was carried out using the system described by Rajput [26]. A dry microscope objective, namely a Nikon CF Plan Achromat 79173, was used to focus the femtosecond laser beam on the surface 160 of the fused silica wafer 140. Energy per pulse of 3.2 μJ was used to open each nanohole 150. The laser-patterned wafer 140 was soaked first in a 5 M KOH solution at 80° C. for 2 hours, and then in de-ionized water also at 80° C. for another 2 hours, in order to remove any machining debris. The washed wafer was dried under a stream of nitrogen, and used as a mold to prepare PLLA membranes for characterization purposes.

A second fused silica mold, designed to prepare PLLA membranes for use in organs-on-a-chip trials was femtosecond laser machined in a similar way. This mold was patterned with a 16 row×100 column rectangular array of surface nanoholes. The distance between rows was 400 while the distance between columns was 100 μm.

Preparation of PVA Nanoneedle Arrays

Recently, Rajput and co-workers reported on a novel method of preparing arrays of freestanding polymer nanoneedles from femtosecond laser patterned fused silica molds using the solution casting mold-replication technique [26]. In the present work, arrays of freestanding polyvinyl alcohol (PVA) nanoneedles (or replicas) 185 were prepared using the water/alcohol-based PVA mold release agent Partall® Film #10 (by Rexco). In particular, each fused silica mold 140 containing an array of surface nanoholes 150 was coated with a thin layer of Partall® Film #10 using a foam paintbrush. The layer was exposed to a flow of nitrogen and allowed to dry. The resulting ~25 μm thick PVA film 180 was peeled-off the fused silica mold 140 and mounted on a 22×22 mm² glass or polyvinyl chloride (PVC) coverslip 145 using double-sided adhesive tape.

Preparation of PLLA Membranes

As shown in FIG. 1, spin coating-assisted deposition of PLLA 190 (molecular weight 100 kDa; 10 mg/mL solution in dichloromethane; Polysciences, Inc.) was performed (at 3000 rpm for 30 s) on PVA nanoneedle arrays, inside a Class 100 clean room. The resulting PLLA films 195 were allowed to dry for 1 minute at 80° C. and stored in polystyrene Petri dishes.

Assembly of Microfluidic Devices

A simple two-compartment device was assembled to test the semipermeable PLLA membranes 100 in an organs-on-a-chip assembly. The device consists of two microfabricated layers 110 in polydimethylsiloxane (PDMS, Sylgard® 184 silicone elastomer kit from Dow Corning, Mich., USA), obtained by SU8 softlithography [27]. Briefly, the bottom layer 110 consists of 16 parallel channels (200 μm width, 100 mm height, 10 mm length), obtained by casting and curing liquid PDMS (10:1) on SU8-2100 mold (from Microchem, MA, USA) fabricated in a Class 100 clean room. The upper chamber was prepared by punching a thick 3 mm layer of PDMS with a sterile disposable 6 mm diameter punch. Ports to access the microfluidic channels were opened by punching 1.59 mm (1/16 inch) diameter holes.

In order to bond a PLLA membrane 195 between the two PDMS layers 110, the channeled PDMS layer 110 was gently pressed against the PLLA layer 195 formed atop a PVA replica 180 as shown in FIG. 1. These two pieces were then immersed in de-ionized water 199 for 6 to 12 hours to allow water to gradually dissolve and remove the sacrificial PVA template 180, leaving behind a semipermeable ultrathin PLLA membrane 100 with precisely patterned micrometer scale pores. The resulting PLLA membrane 100 remained adherent to the channeled PDMS layer 110. The upper PDMS layer 110 chamber and the PLLA membrane 100 were then oxygen-plasma treated (600 mTorr, 100 W, for 45 sec) and finally bonded together. Oxygen-plasma treatment renders the exposed surfaces hydrophilic. Once bonded the devices were immediately filled with deionized sterile water and stored at 4° C. until used.

Loading of Microfluidic Devices

The devices were sterilized by UV irradiation for 30 minutes prior to loading with cell medium and cells. Mimicking seeding protocol used for cell culture in traditional transwell inserts, the water was replaced with full medium, first loading the lower microfluidic channels and then the upper chamber. The nanofilm was not coated with any adhesive protein. The wet device was thus closed in a Petri dish and equilibrated at 37° C. for 12 hours inside the incubator. Cell growth on the PLLA nanofilm was monitored for 7 days as proof of principle.

Cell Culture, Staining and Assays

Human umbilical vein endothelial cells ("HUVECS") [28] were isolated from umbilical cord obtained from a de-identified placenta collected from patients who underwent elective cesarean sections between 37 and 39 weeks of gestation. All procedures related to the consent and collection of tissues were approved by the Vanderbilt University Institutional Review Board. Cells were cultured in EBM-2 media supplemented with 10% of fetal bovine serum (Lonza, USA) and with 1% antibiotics/antimycotics. Purity of the isolation was validated by morphological and immunofluorescent staining for CD31 (DAKO, USA) before loading in the devices. Cells were maintained at 37° C. in a saturated humidity atmosphere containing 95% air/5% $CO_2$, and they were sub-cultured before reaching 70% confluence (approximately every 2 days).

After tripsinization and centrifugation, cells were suspended in full medium (2000 cells/μL) and 50 μL were injected in the device. Medium was refreshed in the device every 2 days.

Vitality was investigated after 7 days in culture by using NucBlue® Live ReadyProbes® Reagent and NucGreen® Dead 488 ReadyProbes® Reagent (Molecular Probes, R37605 and R37109). 20 μL of staining solutions were added directly to cells in full media and incubated for 20 minutes. NucBlue® Live Cell Stain emits at 460 nm when bound to DNA while NucGreen® Dead 488 reagent is a membrane-impermeable stain DNA of dead cells (excitation/emission at 504/523 nm). Cellular cytoskeleton was visualized by F-actin staining using ActinGreen™ 488 ReadyProbes® Reagent from Molecular Probes. Cells were prepared for staining by 4% paraformaldehyde fixation.

Cells were finally observed with an inverted fluorescent microscope (EVOS, FL Cell Imaging System) and with Image J software (Rasband, W. S., ImageJ, U. S. National Institutes of Health, Bethesda, Md., USA).

Results

SEM Characterization of Fused Silica Molds and PVA Replicas

Figure 2A:
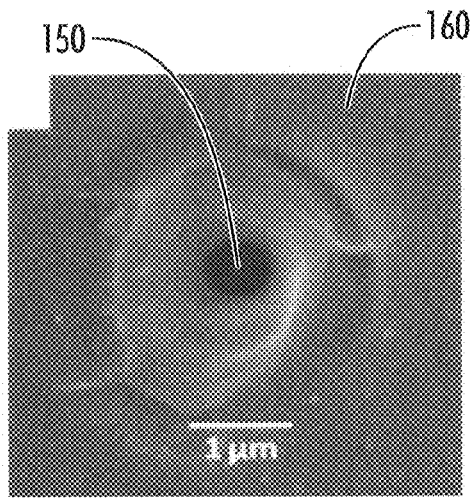
FIG. 2A is an SEM image of a representative femtosecond laser machined nanohole 150 on the surface 160 of a fused silica wafer 140 having a plurality of such nanoholes 150. The nanohole 150 was opened using a single 3.2 µJ, 790 ηm, 160 femtosecond laser pulse.
Figure 2B:
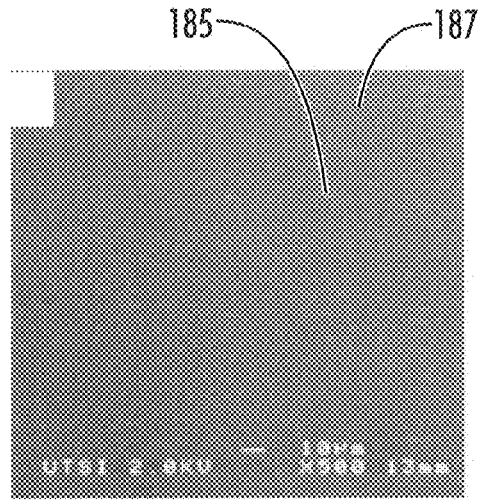
FIG. 2B is an SEM image of the surface 187 of a PVA replica 180 of the surface 160 of the fused silica wafer 140 of FIG. 2A (Pt coated, 45° stage tilt). Replicas of individual nanoholes 150 are referred to herein as "nanoneedles."
Figure 2C:
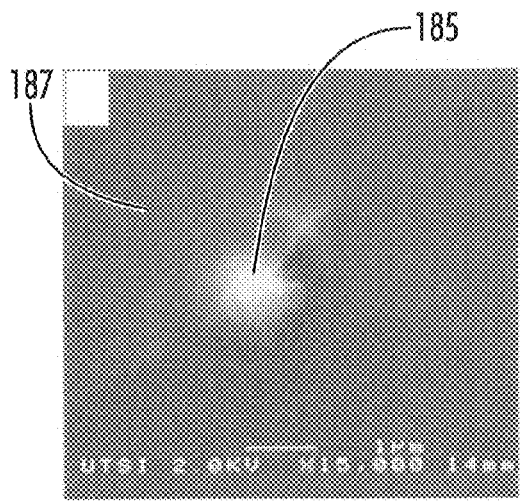
FIG. 2C is an SEM image of a single PVA nanoneedle 185 of FIG. 2B having a final length of 10 µm.
Figure 2D:
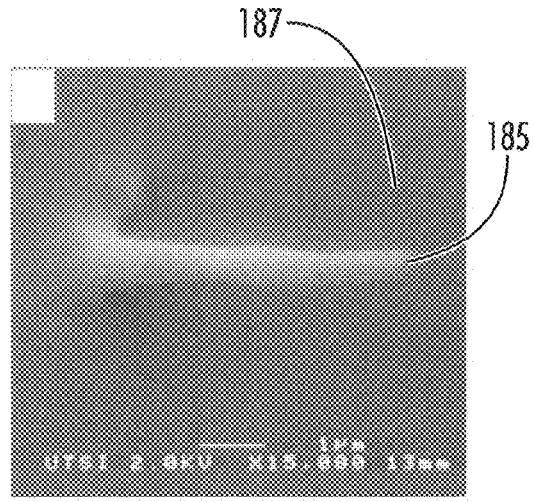
FIG. 2D is an SEM image of the PVA nanoneedle 185 of FIG. 2C at 30° stage tilt.

The surfaces of both the femtosecond laser patterned fused silica mold 140 and the corresponding PVA replica 180 were imaged using a JEOL 6320 field emission scanning electron microscope. Both samples were sputter-coated with a few nanometers of Platinum for successful imaging. An image of a single-pulse femtosecond laser machined nanohole 150 is shown in FIG. 2A. Images of the PVA replica 180, at various magnifications, are shown in FIGS. 2B through 2D.

SEM Characterization of PLLA Membrane

Spin coating assisted deposition of PLLA 190 on PVA replicas 180 was performed using the same processing parameter values used to prepare plain ~100 nm thin PLLA films reported in previous work [29]. As shown in FIG. 1, the PLLA solution 190 spread and coated the full surface 187 of the replica. Due to the high aspect ratio of the PVA nanoneedles 185 and lack of wettability, needles 185 were not completely covered during the spin coating.

Figure 3A:
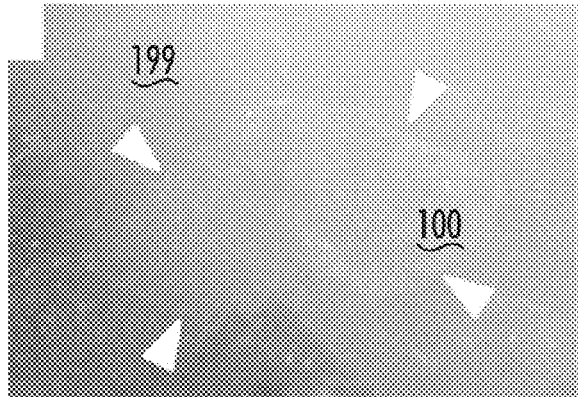
FIG. 3A is an optical photograph of a PLLA film 100 floating on the surface of water 199 after the PVA template has been dissolved using the method of FIG. 1. Film edges are indicated by white arrows.
Figure 3B:
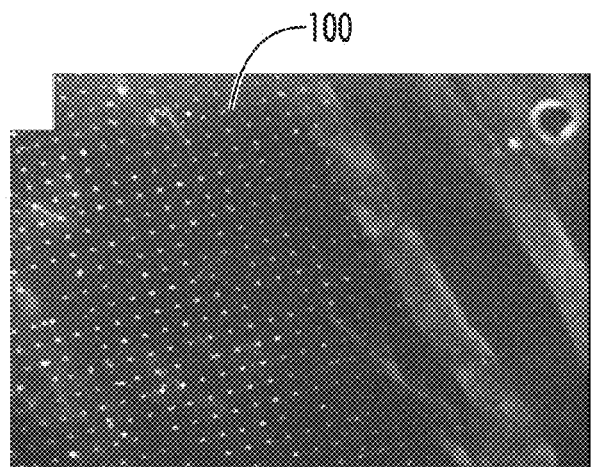
FIG. 3B is an optical microscope image of the PLLA film 100 of FIG. 3A. Pores in the film are shown as white dots.
Figure 3C:
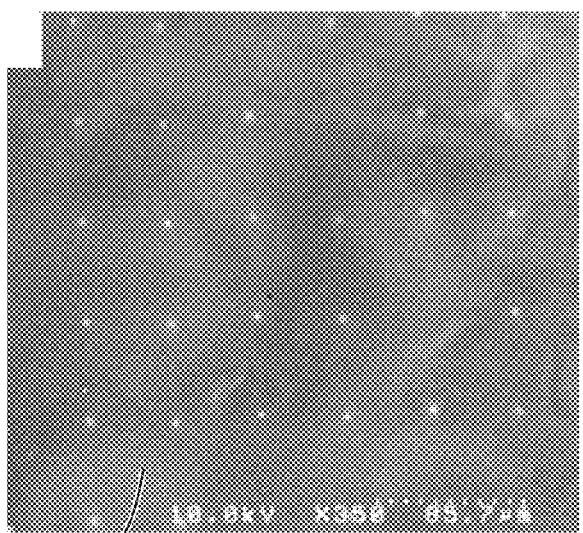
FIG. 3C is an SEM image of the array of pores in the PLLA film 100 of FIG. 3A. A gold coating of 2 nm was used to visualize the pores.
Figure 3D:
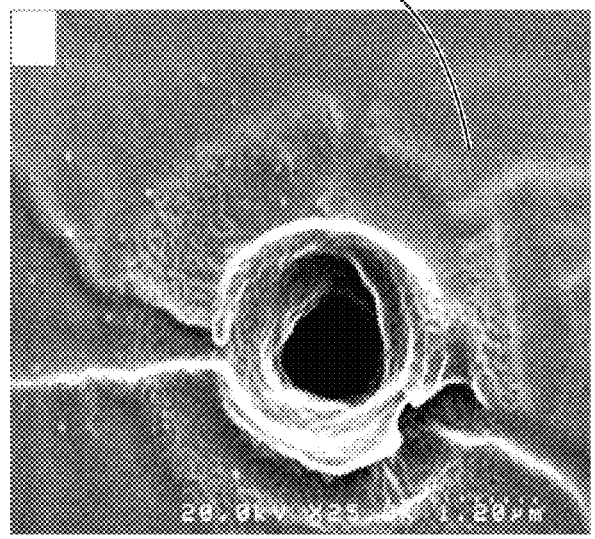
FIG. 3D is an SEM image showing a detail view of a single pore in the film 100 of FIG. 3A.
Figure 4A:
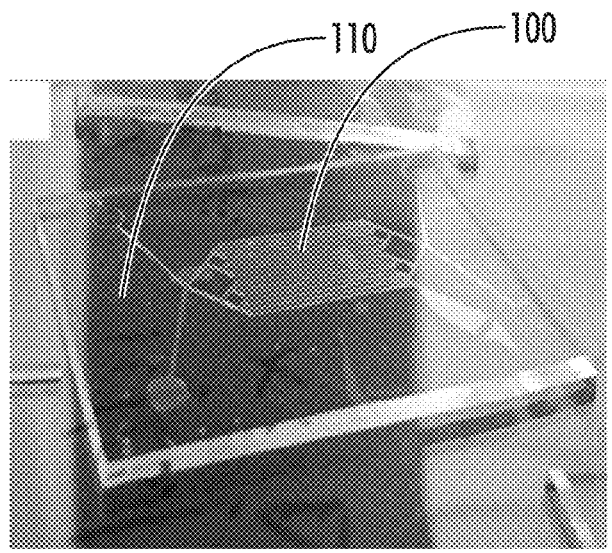
FIG. 4A is a perspective view of the PLLA film 100 of FIG. 3A adhered to the channeled surface of a PDMS layer 110. Microfluidic channels in the surface of the PDMS layer 110 are 200 µm-wide.
Figure 4B:
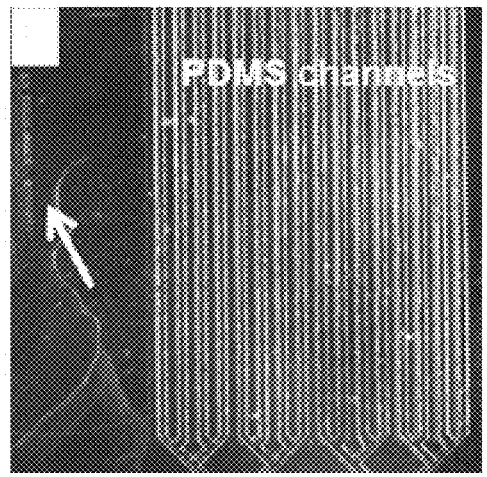
FIG. 4B is a top plan view of the PLLA film 100 and channeled PDMS layer 110 of FIG. 4A. The lateral sample identification label is indicated by a white arrow.
Figure 4C:
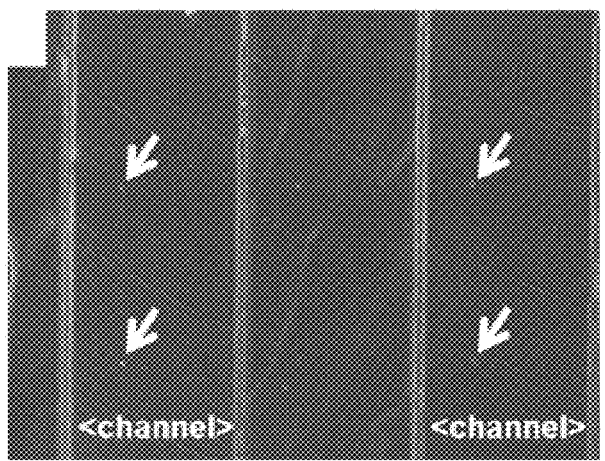
FIG. 4C is a magnified view of the PLLA film 100 and PDMS layer 110 of FIG. 4B showing a group of four micrometric pores (indicated by white arrows) in the PLLA film 100 positioned above the 200 µm-wide microfluidic channels of the PDMS layer 110.
Figure 4D:
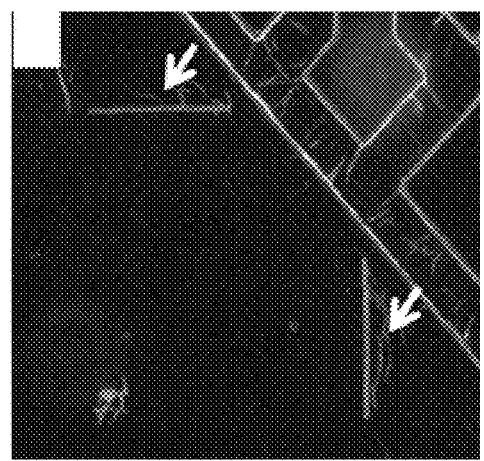
FIG. 4D is another top plan view of the PLLA film 100 and channeled PDMS layer 110 of FIG. 4C with alignment features indicated by white arrows.

The sacrificial layer PVA 180 was dissolved by immersion in de-ionized water 199, and once removed, the PVA needle sites become open pores in the PLLA nanofilm membrane 100. The hydrophobic PLLA film 100 floats freestanding on the water surface 199 (FIG. 3A). The patterned pores can be visualized in bright field once the film 100 is collected and dried on a flat surface, such as a silicon wafer or a glass coverslip (FIGS. 3B and 3C). The PLLA nanofilm 100 replicates perfectly the surface morphology and any irregularity of the PVA replica 180, including the features imposed by the laser in the original silica mold 140 (FIG. 3D).

Different views of a PLLA semipermeable membrane 100 bonded to the bottom channeled PDMS layer 110 are shown in FIGS. 4A through 4D.

The PLLA membrane 100 bonded wrinkle-free to the channeled PDMS layer 110 (see FIGS. 4A-4D). The sixteen rows of micrometric pores of the PLLA membrane 100 aligned precisely above the sixteen microfluidic channels. The sacrificial PVA layer 180 provides a means of handling the nanofilm 195 and mounting the film on the channeled PDMS layer 110 preventing damage to the film; a key concern in manipulation of the ultrathin membrane.

Since both PDMS and PLLA are optically transparent, alignment of various components was done under a stereomicroscope. Together with the pattern of surface pores, the original silica mold 140 has femtosecond laser machined surface alignment marks and a lateral identification label (FIGS. 4B-4D); these microscopic features transfer to the PVA and PLLA films and serve as alignment guides during device assembly.

Figure 5A:
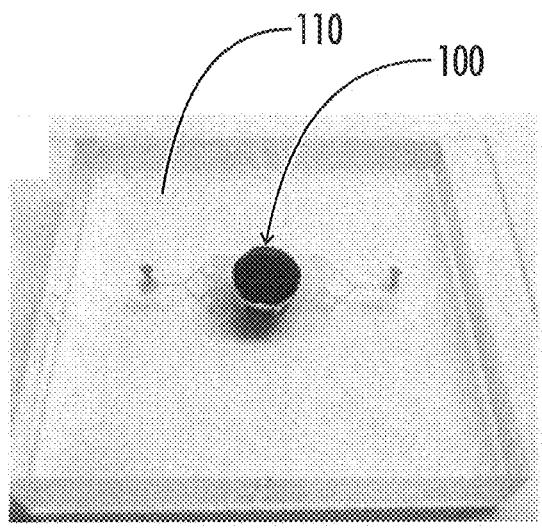
FIG. 5A depicts an embodiment of an assembled multi-chamber microfluidic device typical of perfused organ-on-a-chip devices incorporating a semipermeable ultrathin polymer membrane 100 constructed in accordance with the present disclosure. The upper chamber volume is indicated by blue dye. The lower channeled chamber volume is indicated by red dye.
Figure 5B:
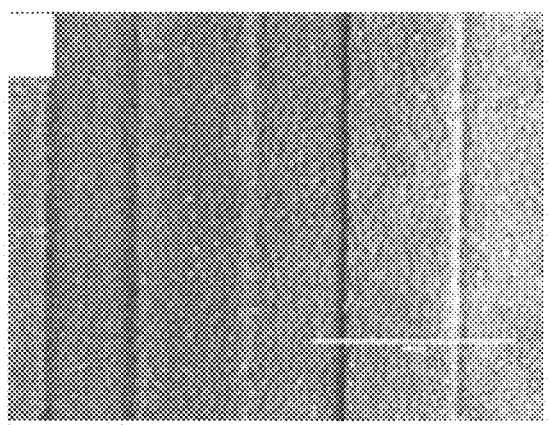
FIG. 5B is an optical differential interference contrast image of HUVECs loaded into the microfluidic device of FIG. 5A at the time of loading (D0, 4×, ph).

We observed that the PLLA membrane 100 tightly adhered to the channeled PDMS layer 110 and did not collapse inside the channels (FIG. 5A). Cells were then seeded directly on the PLLA membrane 100 in the upper chamber without previous coating of the membrane surface. Approximately 100,000 cells were seeded at Day 0 in the device, filling the upper chamber without leakage between the layers. It was possible to observe the cell behavior and monitor growth by optical microscopy due to the transparency of the PLLA membrane in bright field.

Figure 5C:
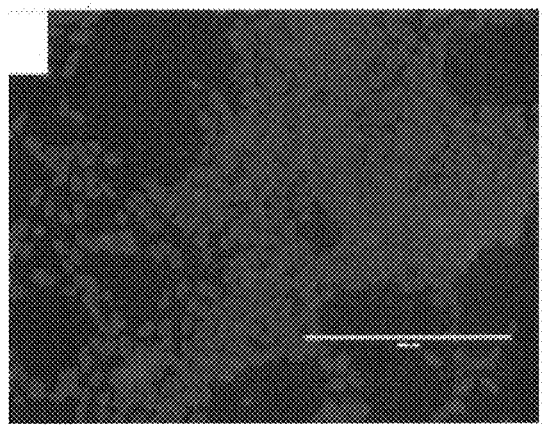
FIG. 5C is an optical fluorescence image of the HUVECs of FIG. 5B stained to differentiate live and dead cells. After seven days the live cells were stained blue and dead cells stained green. Scale bar is 400 µm.
Figure 5D:
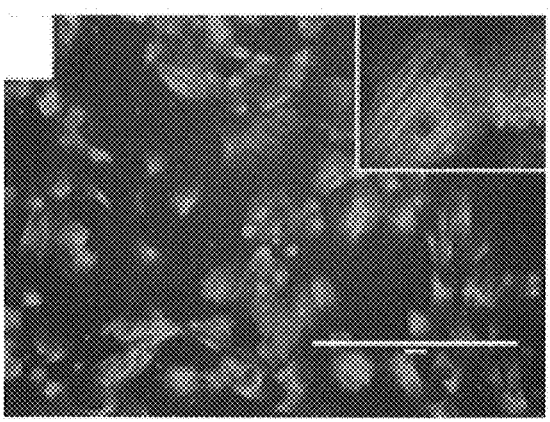
FIG. 5D is an optical fluorescence image of the HUVECs of FIG. 5B subject to actin staining. Actin of HUVECs inside the microfluidic device is stained green. Scale bar is 400 µm. The inset is at 40× magnification.

Oxygen plasma treatment did not adversely affect the biological properties of the PLLA film surfaces; the grow rate and cell morphology of the cells on PLLA inside the device were comparable to the control flask. As shown in FIGS. 5C and 5D, cells proliferate rapidly in the device and with very low mortality (below 1%). The medium of the two chambers was replaced every 48 hours and after 7 days the adhesion of the cells on the semipermeable PLLA membrane was confirmed by F-actin staining (FIG. 5D). The media from the two chambers were collected and the amount of cells in the two chambers was measured by using a cell counter. Cells were found only in medium from the upper chamber, thus proving that the size of the pores did not exceed the nominal value of 1 μm in diameter (data not shown). At the same time, permeability of the membrane was confirmed by 150 kDa FITC-dextran diffusion measurements.

Permeability of the PLLA Nanofilms

Diffusion of FITC dextran (70 kDa molecular weight, Sigma Aldrich, USA) through the perforated PLLA membranes was measured by using a UV-Vis Spectrophotometer (Varian Cary 50, Agilent Technologies, Santa Clara, Calif.).

Figure 6:
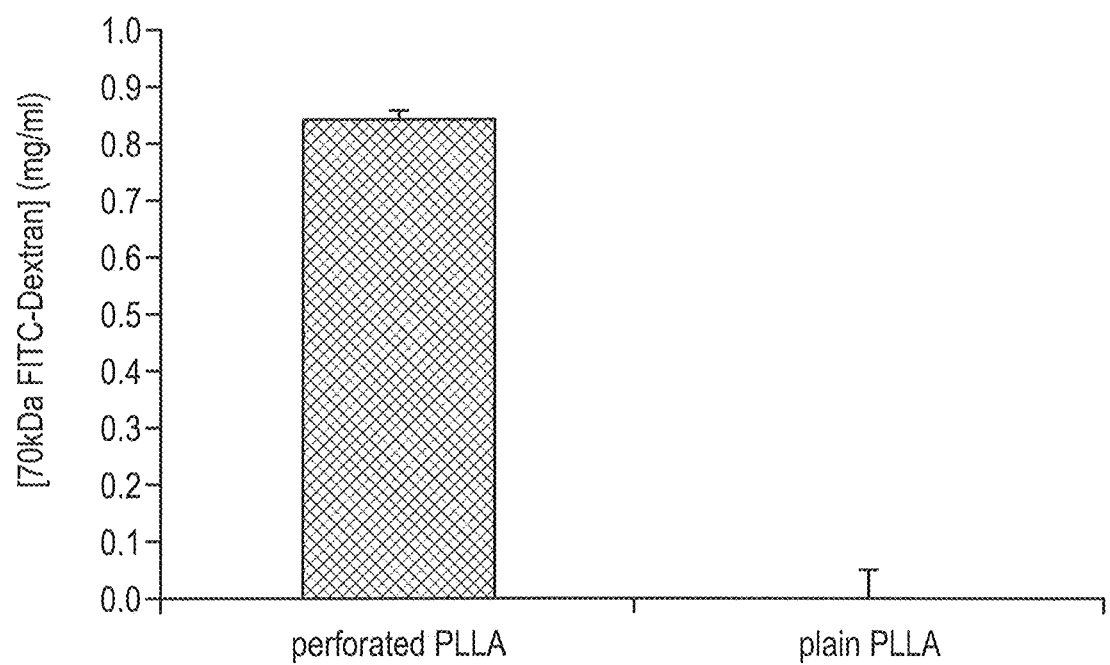
FIG. 6 is a bar graph showing the relative permeability to FITC-dextran of a perforated semipermeable ultrathin PLLA membrane constructed in accordance with the present disclosure (left bar) and a non-perforated PLLA control membrane (right bar).

The experiment was performed in a 96-well plate. Five devices were assembled, following the protocols described above in the Materials and Methods section, each one integrating one PLLA perforated membrane. FITC dextran solution (2 mg/mL in MilliQ water) was used to fill the upper chamber of the device, while the lower channels were filled with MilliQ water. Liquid from the lower channels was collected after 6 hours. One additional device was assembled with a PLLA membrane prepared with the same process parameters on a flat silicon wafer, which thus did not have holes and was not permeable. The relative permeability to FITC-dextran of perforated PLLA membranes and a non-perforated PLLA control membranes are shown in FIG. 6.

DISCUSSION AND CONCLUSIONS

Fabrication of biocompatible, transparent, semipermeable ultrathin polymer membranes with precisely patterned micropores is difficult by perforation using e-beam lithography, focused ion beam milling, or laser micromachining, all of which processes lack production scalability. Forming membranes using a molding approach is also difficult to implement. First of all, the polymer melt, polymer precursor, or the polymer-solvent solution being used must have sufficiently low viscosity to spread and fill the surface of the mold completely and homogeneously, without leaving a residual layer on top of the mold nanoneedles or micropillars. Mechanical peeling of the resulting membrane is also problematic because the thinness of the membrane makes it very delicate and susceptible to tearing during removal from the mold. Once released from the mold, the membrane must also be transferred and precisely attached to the microfluidic device and without any wrinkles or folds.

The method reported herein provides a quick, repeatable and convenient route to prepare multiple copies of the semipermeable membranes having an engineered porosity. First, the direct one-step femtosecond laser machining of the fused silica molds can be carried out at kilohertz rates. With the current system, this translates to patterning a regular array of four million surface nanoholes inside a one square centimeter area in less than one hour. Molds can be prepared with a distance between nanoholes as small as 2 μm. Chemically inert and mechanically hard, the fused silica mold 140 can be used to prepare thousands of PVA replicas 180. The PVA formulation used does not stick to fused silica. Each PVA replica 180 precisely and repeatedly duplicates all the features of the mold, yielding straight, standing, and aligned high aspect-ratio nanoneedles 185. PVA replicas 180 can be produced relatively quickly (15-30 minutes) and the mold 140 can be easily cleaned from residual traces of PVA by hot water. The water-solubility and organic solvent-resistance of PVA makes it a suitable sacrificial material to use as template in preparing semipermeable membranes for many organic solvent-soluble polymers of interest. Finally, the PVA template 180 provides a convenient vehicle to transfer, align and attach the ultrathin membrane 100 to the microfluidic device without introducing undesirable wrinkles or folds in the final assembly.

While the selection of biocompatible polymers is wide and the fabrication of films with micrometric thickness can be achieved with several methods, handling of perforated thin membrane represents a technological challenge. In this work we selected PLLA since its biocompatibility is well demonstrated. Furthermore, the sacrificial layer is fundamental for handling and positioning of the ultrathin membrane: while a plain sacrificial layer is traditionally used to release positioning polymeric films from their support, for example in stretchable and epidermal electronics [30, 31], in this case the dissolvable PVA includes not only the needles but also temporary labels and frames to align the pattern of needles with the microfabricated channels in the PDMS.

The semipermeable property of the PLLA membranes disclosed herein guarantees the possibility to separate two fluidic compartments and to select the size of particulates (i.e. cells) able to pass through membrane pores. This is a key characteristic in lab-on-a-chip technology, where cells extravasation and passage of chemical species between communicating compartments need to be controlled. Organs-on-a-chip seeks to understand complex processes; e.g. organ development, embryogenesis, tumor metastasis, and leukocyte infiltration that are regulated by cellular responses to multiple (competing) chemokines as well as autocrine feedback loops, cell-cell interactions, and mechanical stress. The result outlined herein of a scalable, tunable semipermeable nanofilm membrane will contribute to the success of organs-on-a-chip models and enable more faithful recapitulation of in vivo conditions.

The invention has been described in connection with what are presently considered to be the most practical and preferred embodiments. However, the present invention has been presented by way of illustration and is not intended to be limited to the disclosed embodiments. Accordingly, those skilled in the art will realize that the invention is intended to encompass all modifications and alternative arrangements within the spirit and scope of the invention as set forth in the appended claims.

Throughout this document, various references are mentioned. All such references are incorporated herein by references, including the references set forth in the following list:

REFERENCES

1. Boyden, S., The chemotactic effect of mixtures of antibody and antigen on polymorphonuclear leucocytes. *The Journal of Experimental Medicine* 1962, 115 (3), 453-466.

2. Ingber, D. E., Reverse Engineering Human Pathophysiology with Organs-on-Chips. *Cell* 164 (6), 1105-1109.
3. Huh, D.; Hamilton, G. A.; Ingber, D. E., From 3D cell culture to organs-on-chips. *Trends in Cell Biology* 21 (12), 745-754.
4. McCaffrey, L. M.; Macara, I. G., Epithelial organization, cell polarity and tumorigenesis. *Trends in Cell Biology* 21 (12), 727-735.
5. Okamura, Y.; Kabata, K.; Kinoshita, M.; Saitoh, D.; Takeoka, S., Free-Standing Biodegradable Poly(lactic acid) Nanosheet for Sealing Operations in Surgery. *Advanced Materials* 2009, 21 (43), 4388-+.
6. Fujie, T.; Okamura, Y.; Takeoka, S., Selective surface modification of free-standing polysaccharide nanosheet with micro/nano-particles identified by structural color changes. *Colloids and Surfaces A: Physicochemical and Engineering Aspects* 2009, 334 (1-3), 28-33.
7. Markutsya, S.; Jiang, C. Y.; Pikus, Y.; Tsukruk, V. V., Freely suspended layer-by-layer nanomembranes: Testing micromechanical properties. *Advanced Functional Materials* 2005, 15 (5), 771-780.
8. Zucca, A.; Yamagishi, K.; Fujie, T.; Takeoka, S.; Mattoli, V.; Greco, F., Roll to roll processing of ultraconformable conducting polymer nanosheets. *Journal of Materials Chemistry C* 2015, 3 (25), 6539-6548.
9. Taccola, S.; Desii, A.; Pensabene, V.; Fujie, T.; Saito, A.; Takeoka, S.; Dario, P.; Menciassi, A.; Mattoli, V., Free-Standing Poly(L-lactic acid) Nanofilms Loaded with Superparamagnetic Nanoparticles. *Langmuir* 2011, 27 (9), 5589-5595.
10. Jiang, C. Y.; Tsukruk, V. V., Freestanding nanostructures via layer-by-layer assembly. *Advanced Materials* 2006, 18 (7), 829-840.
11. Endo, H.; Kado, Y.; Mitsuishi, M.; Miyashita, T., Fabrication of free-standing hybrid nanosheets organized with polymer Langmuir-Blodgett films and gold nanoparticles. *Macromolecules* 2006, 39 (16), 5559-5563.
12. Cho, J.; Char, K.; Hong, J. D.; Lee, K. B., Fabrication of highly ordered multilayer films using a spin self-assembly method. *Advanced Materials* 2001, 13 (14), 1076-+.
13. Ricotti, L.; Taccola, S.; Pensabene, V.; Mattoli, V.; Fujie, T.; Takeoka, S.; Menciassi, A.; Dario, P., Adhesion and proliferation of skeletal muscle cells on single layer poly(lactic acid) ultra-thin films. *Biomedical Microdevices* 2010, 12 (5), 809-819 11p.
14. Ricotti, L.; Taccola, S.; Bernardeschi, I.; Pensabene, V.; Dario, P.; Menciassi, A., Quantification of growth and differentiation of C2Cl2 skeletal muscle cells on PSS-PAH-based polyelectrolyte layer-by-layer nanofilms. *Biomedical Materials* 2011, 6 (3).
15. Kim, H. J.; Ingber, D. E., Gut-on-a-Chip microenvironment induces human intestinal cells to undergo villus differentiation. *Integrative Biology* 2013, 5 (9), 1130-1140.
16. Kim, H. J.; Huh, D.; Hamilton, G.; Ingber, D. E., Human gut-on-a-chip inhabited by microbial flora that experiences intestinal peristalsis-like motions and flow. *Lab on a Chip* 2012, 12 (12), 2165-2174.
17. Booth, R.; Kim, H., Characterization of a microfluidic in vitro model of the blood-brain barrier (mu BBB). *Lab on a Chip* 2012, 12 (10), 1784-1792.
18. Esch, M. B.; Sung, J. H.; Yang, J.; Yu, C. H.; Yu, J. J.; March, J. C.; Shuler, M. L., On chip porous polymer membranes for integration of gastrointestinal tract epithelium with microfluidic 'body-on-a-chip' devices. *Biomedical Microdevices* 2012, 14 (5), 895-906.
19. Ulbricht, M., Advanced functional polymer membranes. *Polymer* 2006, 47 (7), 2217-2262.
20. Uragami, T.; Naito, Y.; Sugihara, M., Studies on synthesis and permeability of special polymer membranes 0.39. permeation characteristics and structure of polymer blend membranes from poly(vinylidene fluoride) and poly (ethylene glycol). *Polymer Bulletin* 1981, 4 (10), 617-622.
21. Martin, C. R.; Nishizawa, M.; Jirage, K.; Kang, M., Investigations of the transport properties of gold nanotubule membranes. *Journal of Physical Chemistry B* 2001, 105 (10), 1925-1934.
22. Kim, M. J.; Wanunu, M.; Bell, D. C.; Meller, A., Rapid fabrication of uniformly sized nanopores and nanopore arrays for parallel DNA analysis. *Advanced Materials* 2006, 18 (23), 3149-+.
23. Kuiper, S.; van Rijn, C. J. M.; Nijdam, W.; Elwenspoek, M. C., Development and applications of very high flux microfiltration membranes. *Journal of Membrane Science* 1998, 150 (1), 1-8.
24. Adiga, S. P.; Jin, C. M.; Curtiss, L. A.; Monteiro-Riviere, N. A.; Narayan, R. J., Nanoporous membranes for medical and biological applications. *Wiley Interdisciplinary Reviews-Nanomedicine and Nanobiotechnology* 2009, 1 (5), 568-581.
25. White, Y. V.; Li, X. X.; Sikorski, Z.; Davis, L. M.; Hofmeister, W., Single-pulse ultrafast-laser machining of high aspect nano-holes at the surface of $SiO_2$. *Optics Express* 2008, 16 (19), 14411-14420.
26. Rajput, D.; Costa, L.; Lansford, K.; Terekhov, A.; Hofmeister, W., Solution-Cast High-Aspect-Ratio Polymer Structures from Direct-Write Templates. *ACS Appl. Mater. Interfaces* 2013, 5 (1), 1-5.
27. Optofluidics: fundamentals, devices, and applications. New York: McGraw-Hill: New York, 2010.
28. Baudin, B.; Bruneel, A.; Bosselut, N.; Vaubourdolle, M., A protocol for isolation and culture of human umbilical vein endothelial cells. *Nature Protocols* 2007, 2 (3), 481-485.
29. Pensabene, V.; Patel, P. P.; Williams, P.; Cooper, T. L.; Kirkbride, K. C.; Giorgio, T. D.; Tulipan, N. B., Repairing Fetal Membranes with a Self-adhesive Ultrathin Polymeric Film: Evaluation in Mid-gestational Rabbit Model. *Annals of Biomedical Engineering* 2015, 43 (8), 1978-1988.
30. Jeong, J. W.; Yeo, W. H.; Akhtar, A.; Norton, J. J. S.; Kwack, Y. J.; Li, S.; Jung, S. Y.; Su, Y. W.; Lee, W.; Xia, J.; Cheng, H. Y.; Huang, Y. G.; Choi, W. S.; Bretl, T.; Rogers, J. A., Materials and Optimized Designs for Human-Machine Interfaces Via Epidermal Electronics. *Advanced Materials* 2013, 25 (47), 6839-6846.
31. Zucca, A.; Cipriani, C.; Sudha; Tarantino, S.; Ricci, D.; Mattoli, V.; Greco, F., Tattoo Conductive Polymer Nanosheets for Skin-Contact Applications. *Advanced Healthcare Materials* 2015, 4 (7), 983-990.

What is claimed is:

1. A method of fabricating a semipermeable polymer membrane, consisting of:
   providing a mold having a patterned array of nanoholes femtosecond laser ablated in a surface of the mold;
   applying a first polymer solution onto the surface of the mold whereby the first polymer solution infiltrates the nanoholes;
   drying the first polymer solution to form a negative replica of the mold, the replica having a first surface, a second surface opposite the first surface, and a plurality of freestanding nanoneedles extending a nanoneedle height from the first surface;

removing the replica from the mold;

coating the first surface of the replica with a second polymer solution, whereby the first surface of the replica is covered with a layer of the second polymer solution having a thickness less than the nanoneedle height such that the nanoneedles extend through the layer of the second polymer solution;

drying the second polymer solution to form a porous polymer film; and dissolving the replica in a solvent to release the porous polymer film from the replica.

2. The method of claim 1, wherein:

the porous polymer film has a thickness of less than one micron; and the first surface of the replica is coated with a second polymer solution by spin-coating assisted deposition.

* * * * *